United States Patent
Rosensweet et al.

(10) Patent No.: US 11,576,920 B2
(45) Date of Patent: *Feb. 14, 2023

(54) COMPOSITION AND METHOD TO AID IN HORMONE REPLACEMENT THERAPY

(71) Applicants: Daved Rosensweet, Longboat Key, FL (US); Joshua B. Rosensweet, Longboat Key, FL (US)

(72) Inventors: Daved Rosensweet, Longboat Key, FL (US); Joshua B. Rosensweet, Longboat Key, FL (US)

(73) Assignee: The Menopause Method, Inc., Sarasota, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/846,487

(22) Filed: Apr. 13, 2020

(65) Prior Publication Data

US 2020/0297738 A1  Sep. 24, 2020

Related U.S. Application Data

(63) Continuation-in-part of application No. 16/355,935, filed on Mar. 18, 2019, now Pat. No. 10,660,905.

(51) Int. Cl.
| | |
|---|---|
| *A61K 31/57* | (2006.01) |
| *A61K 47/44* | (2017.01) |
| *A61K 31/568* | (2006.01) |
| *A61K 47/46* | (2006.01) |
| *A61K 9/107* | (2006.01) |

(52) U.S. Cl.
CPC ............ *A61K 31/57* (2013.01); *A61K 31/568* (2013.01); *A61K 47/44* (2013.01); *A61K 47/46* (2013.01); *A61K 9/107* (2013.01)

(58) Field of Classification Search
CPC ..................................................... A61K 31/57
See application file for complete search history.

(56) References Cited

U.S. PATENT DOCUMENTS

| | | | |
|---|---|---|---|
| 6,623,761 B2 | 9/2003 | Hassan | |
| 8,048,920 B2 | 11/2011 | Joerger | |
| 8,435,561 B2 | 5/2013 | Besins | |
| 8,512,718 B2 | 8/2013 | Eini | |
| 8,614,278 B2 | 12/2013 | Loubert | |
| 8,734,855 B2 | 5/2014 | Liu | |
| 8,883,156 B2 | 11/2014 | Wan | |
| 8,901,088 B2 | 12/2014 | Kim | |
| 8,916,153 B2 | 12/2014 | Wan | |
| 8,952,070 B2 | 2/2015 | Lindahl | |
| 9,096,666 B2 | 8/2015 | Wan | |
| 9,149,534 B2 | 10/2015 | Leshchiner | |
| 9,365,532 B1 | 6/2016 | Isaacman | |
| 10,285,998 B1 * | 5/2019 | Rosensweet | ......... A61K 31/565 |
| 10,660,905 B2 * | 5/2020 | Rosensweet | ............ A61K 9/10 |

FOREIGN PATENT DOCUMENTS

| | | |
|---|---|---|
| EP | 2621517 B1 | 6/2015 |
| EP | 2821056 A1 | 7/2015 |
| EP | 2821080 A1 | 7/2015 |
| WO | 2011074015 A2 | 6/2011 |
| WO | 2011080716 A2 | 7/2011 |
| WO | 2012037000 A1 | 3/2012 |
| WO | 2014037343 A1 | 3/2014 |
| WO | 2014078590 A1 | 5/2014 |
| WO | 2015136106 A1 | 9/2015 |
| WO | 2016203025 A1 | 12/2016 |
| WO | 2017123485 A1 | 7/2017 |
| WO | 2017177265 A1 | 10/2017 |

* cited by examiner

*Primary Examiner* — Rei Tsang Shiao
(74) *Attorney, Agent, or Firm* — Da Vinci's Notebook, LLC

(57) ABSTRACT

A pharmaceutical two-phase admixture for topical application, transdermal or transmucosal, characterized by components in two phases, a liquid and a solid, adapted for topical application, transdermal or transmucosal, to various skin and/or mucosal surface areas of the body is disclosed. The solid phase is comprised of one or more bio-identical hormones and the liquid phase is comprised of one or more excipient carrier oils. The bio-identical hormone component is comprised of one or more of Bi-Est, testosterone, progesterone, and dehydroepiandrosterone. The excipient carrier oil component is comprised of one or more of a wide range of common and rare pharmacological oils including specific formulations of jojoba oil, evening primrose oil, and borage seed oil. The solid phase bio-identical hormone component is comprised of either a standard coarse formulation or a formulation comprised of nanoparticles. The pharmaceutical admixture is especially useful in a regime of hormone replacement therapy.

13 Claims, 3 Drawing Sheets

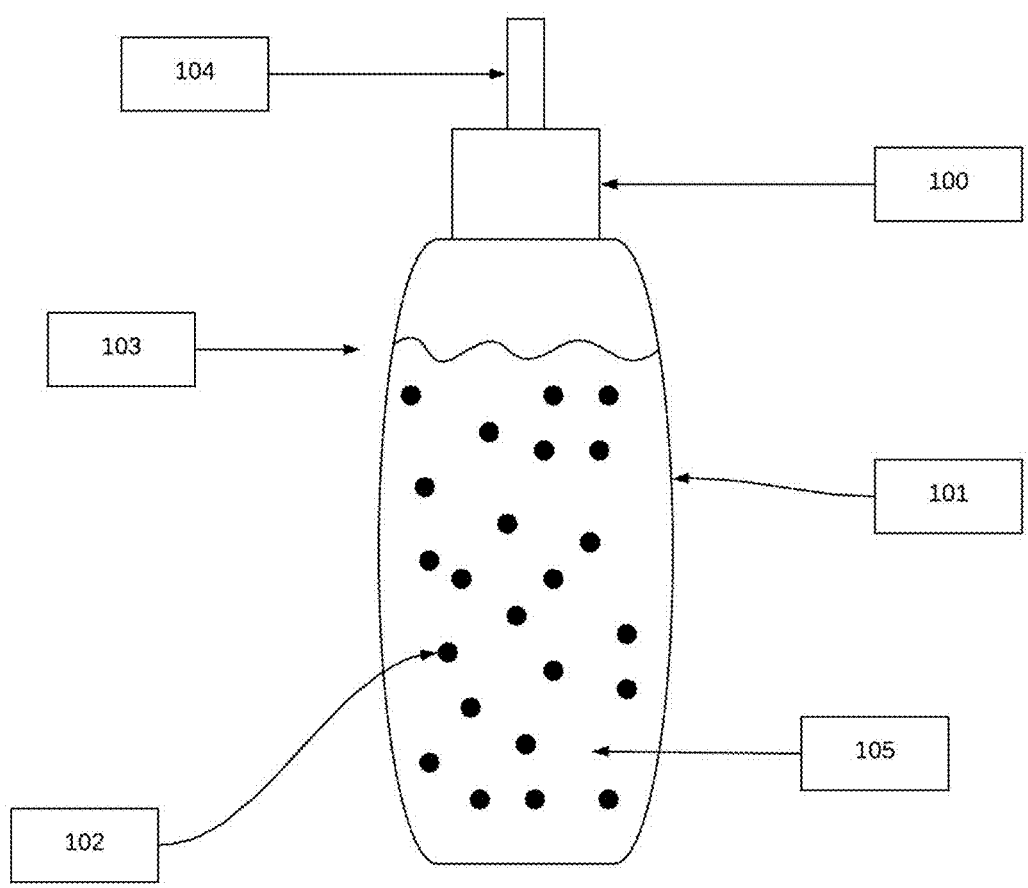
Figure 1 – Dispersed Phase

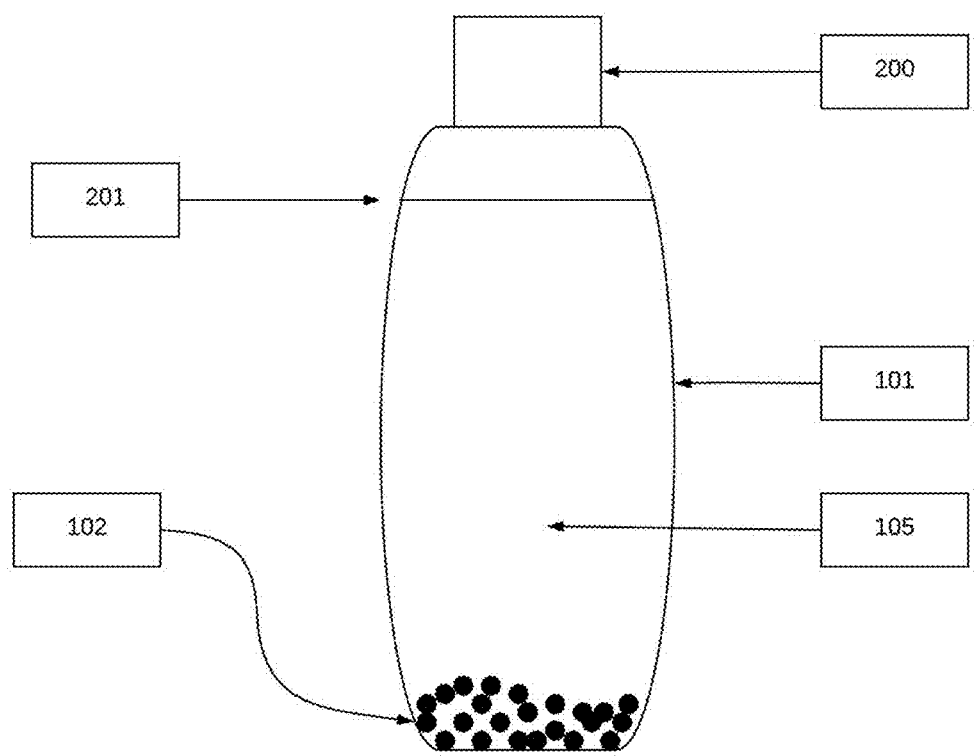

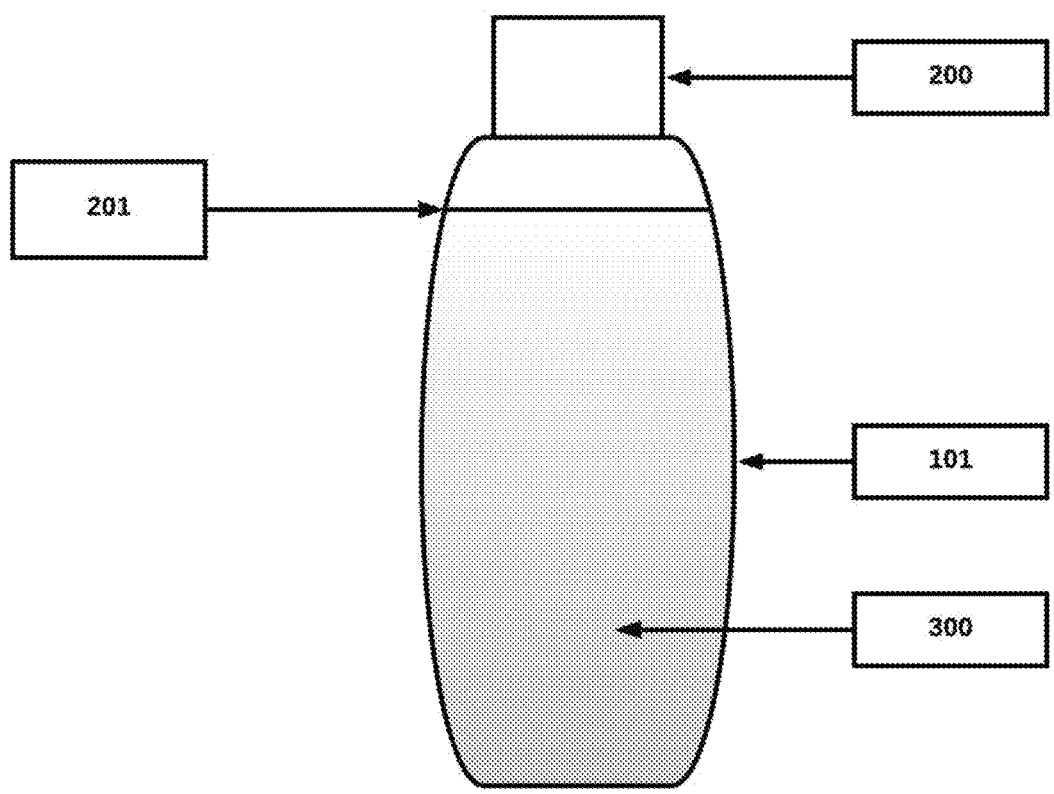
Figure 3 – Nanoparticle Dispersion

COMPOSITION AND METHOD TO AID IN HORMONE REPLACEMENT THERAPY

CROSS-REFERENCE TO RELATED APPLICATIONS

This patent application is a Continuation-In-Part of the U.S. Non-Provisional application Ser. No. 16/355,935 filed Mar. 18, 2018 (now pending), which is a Divisional of U.S. Non-provisional application Ser. No. 15/944,842 filed Apr. 4, 2018 (now U.S. Pat. No. 10,285,998 B1) the disclosures of which are incorporated by reference in their entirety.

FIELD OF THE INVENTION

This disclosure of two-phase admixtures and methodology relates to hormone replacement therapy.

BACKGROUND OF THE INVENTION

As noted in U.S. Pat. No. 6,228,852B1,
"Progesterone is a steroid hormone that is produced by the ovaries during a woman's child-bearing years. Progesterone is also made, although in smaller amounts, by the adrenal glands in both sexes and by the testes in males. An astonishing variety of physiological functions are mediated by progesterone (See e.g., Lee, 1993, Natural Progesterone, BLL Publishing, Sebastopol, Calif.). For example, progesterone, which surges following ovulation, maintains the secretory endometrium and thus, helps to ensure the survival of the embryo and fetus. It also acts as a diuretic, an antidepressant, and as a precursor of corticosteroids and of other sex hormones, notably estrogen and testosterone. There is also evidence that progesterone affords protection against loss of libido, osteoporosis, endometrial cancer, breast cancer, and fibrotic cysts."

As women age, they experience a decline in the production of progesterone, estrogens and androgens. In addition to uncomfortable symptoms, such as hot flashes, sleep disturbance, and cognitive challenges, which are frequently experienced at around the time of menopause, there is an increase in the prevalence of debilitating conditions, including heart disease, loss of skeletal muscle, osteoporosis, cognitive decline and the possibility of stroke.

At present, a common form of treatment for many of the above conditions is oral administration of estrogen. In addition to oral administration, estrogen may be introduced to the body by a vaginal suppository, intramuscular injection, buccal mucosa pouch and in sublingual troches, transdermal patch, creams and gels, nasal mucosal spray, and subcutaneous implant. In a similar manner to estrogen, other hormones such as progesterone, testosterone, and dehydroepiandrosterone (DHEA) may be administered as active pharmacological ingredients in support of a hormone replacement therapy regime. However, there is the possibility of substantial adverse systemic side effects arising from the misuse of any of these replacement hormones. These adverse effects include possible contributions to endometrial hyperplasia, endometrial carcinoma, breast cancer, thrombophlebitis, pulmonary embolism, cerebral thrombosis, mental depression, nausea, insomnia, fluid retention, migraine headache, liver dysfunction, weight gain, acne and more.

In addition to systemic side effects, there are specific local side effects associated with the method of administration. U.S. Pat. No. 8,026,228 teaches oral administration of hormones, but due to gastrointestinal degradation of the drug and the "first pass effect" in the liver, oral administration of estrogens requires higher than medically necessary doses to obtain the proper therapeutic level in the body thus possibly elevating the probability of systematic side effects. U.S. Pat. No. 8,629,129 teaches the use of vaginal suppositories which can, if the woman is having intercourse, be transmitted to her partner. Suppositories can also cause irritation due to a high local drug concentration, and can have a tendency to dislodge and exit the vagina during activity. U. S. Publication. No. 2005/0282749 teaches administration via intramuscular injection, but such administration may require a visit to a medical facility, is inconvenient for frequent doses, and can cause site injection irritation due to a high local drug concentration. This method, as well as pellet injection, does not allow for minor dosage alterations based upon symptoms of insufficiency or excess varying with actual day to day needs. U.S. Pat. No. 7,951,398 teaches transdermal patches, which while popular, require the diffusion of drugs across a limited surface area that can cause irritation due to a high drug concentration, and furthermore, penetration enhancers, often used in transdermal patches, can also cause skin irritation. U.S. Pat. No. 6,117,446 teaches buccal administration to the mucosal membranes of the mouth, but such administration can lead to significant quantities of the hormones being swallowed, thus subject to the "first pass effect." It can also lead to high drug concentration irritation like other methods. PCT Publication No. WO1998006404 teaches using a subcutaneous implant, but such administration requires a visit to a medical facility and does not lend itself well to monthly breaks or mini-variations in hormonal dosage needs as is common. Also, it is inconvenient for frequent doses, and furthermore, the implant site is subject to irritation due to a localized concentration of the drug. Additionally, if required, the removal of the implant may prove to be difficult. U. S. Publication No. 2006/0147385 teaches the use of nasal mucosal spray, but such application requires a high drug concentration due to the short application time, has a rapid absorption time thus producing excessive hormonal dosage peaks, and is likewise subject to induce local irritation. U. S. Publication No. 2004/0266688 teaches intravenous administration, but such administration requires excessively frequent visits to a medical facility, as well as also producing unphysiological hormonal dosage peaks, and is inconvenient for frequent doses.

SUMMARY OF THE INVENTION

An object of the two-phase admixtures and methodology disclosed herein is to solve or at least significantly improve upon the deficiencies of the prior art noted above.

One aspect of the two-phase admixtures and methodology disclosed herein there is provided a two-phase admixture comprised of two phases, a liquid and a solid, where the liquid phase is primarily comprised of one or more excipient carrier oils and the solid phase is comprised of one or more bio-identical hormone formulations useful in hormone replacement therapy.

Another aspect of the two-phase admixtures and methodology disclosed herein there is provided a method of preparing the two-phase bio-identical hormone admixture above for use by a female or male patient. This method is appropriately practiced by licensed compounding pharmacists.

Yet, another aspect of the two-phase admixtures and methodology disclosed herein there is provided a method of preparing a series of pharmacy-ready two-phase bio-identical hormone admixtures of varying concentrations of bio-identical hormones such that a hormone replacement therapy involving a pharmaceutical effective dose of one or more bio-identical hormones can be prescribed by a doctor and filled by a regular pharmacist.

Still, yet another aspect of the two-phase admixtures and methodology disclosed herein there is provided the incorporation of solid phase bio-identical hormone formulations composed of nanoparticles such that the final two-phase admixtures can be prepared as long-term stable dispersions requiring less agitation to properly prepare for application.

Still, another aspect of the two-phase admixtures and methodology disclosed herein there is provided a method of self-application of the above two-phase bio-identical hormone admixture to the appropriate parts of the female or male patient's skin and mucous membranes.

Further objects, features, and advantages of the present application will be apparent to those skilled in the art from detailed consideration of the embodiments that follow.

BRIEF DESCRIPTION OF THE DRAWINGS

FIG. 1 is a schematic front view of the dispensing bottle body 101 showing a temporarily dispersed solid bio-identical hormone composed of coarse particles 102 in excipient carrier oil 105. The said dispensing bottle body 101 is capped by a dispensing cap 100 which contains an orifice reducer 104. Said orifice reducer 104 has an inside diameter appropriate to dispense drops of a specific volumetric quantity of the two-phase bio-identical hormone admixture. The surface of the two-phase bio-identical hormone admixture in the dispensing bottle 101 is indicated by the wavy surface line 103. Surrounding the temporarily dispersed solid bio-identical hormone composed of coarse particles 102 is the excipient carrier oil 105 comprised of one or more oils. This is the expected state of the two-phase bio-identical hormone admixture just after agitation and just prior to self-application by the female or male patient where the solid bio-identical hormone composed of coarse particles 102 has been temporarily dispersed in the excipient carrier oil 105.

FIG. 2 is a schematic front view of the dispensing bottle body 101 showing the settled solid bio-identical hormone composed of coarse particles 102 at the bottom of the dispensing bottle body 101. The excipient carrier oil 105 for the most part remains above the solid bio-identical hormone composed of coarse particles 102. The said dispensing bottle body 101 is sealed by a sealing cap 200 which fits over the dispensing cap 100 and the orifice reducer 104. The surface of the two-phase bio-identical hormone admixture in the dispensing bottle 101 is indicated by the horizontal straight line surface line 201. This is the expected state of two-phase bio-identical hormone admixture in storage and prior to the application of agitation to temporarily suspend the solid bio-identical hormone composed of coarse particles 102 in the liquid excipient carrier oil 105 comprised of one or more oils.

FIG. 3 is a schematic front view of the dispensing bottle body 101 with the sealing cap 200 and the surface line 201 showing the dispersion of a solid bio-identical hormone composed of nanoparticles 300. When properly agitated in the liquid phase excipient carrier oil 105 the solid bio-identical hormone composed of nanoparticles 300 produces a long-term stable dispersion which significantly enhances the precision with which drops of the two-phase admixture can be produced. The vertical shading of the representation of the solid bio-identical hormone composed of nanoparticles 300 which is darker at the bottom with increasing vertical lightness indicates that some settling of the solid bio-identical hormone composed of nanoparticles 300 may occur.

DETAILED DESCRIPTION OF THE PREFERED EMBODIMENT

While the present two-phase admixtures and methodology are disclosed with respect to the preferred embodiments described below and in the figures, the present two-phase admixtures and methodology are limited only by the metes and bounds of the claims that follow.

The two-phase admixtures and methodology disclosed herein offer a significantly improved approach to hormone replacement therapy. This approach offers increased safety, minimizing the possibility of adverse side effects because of the two phase delivery system, suspending the bio-identical hormones in oil(s), and thus eliminating the need to use toxic solvents to bring hormones into solution. This approach also offers greater flexibility in terms of delivering, via drops, the amounts of individual bio-identical hormones as well as minimizing the likelihood of localized, application site specific adverse side effects.

For a general understanding of the disclosed two-phase admixtures and methodology, reference is made to the drawings. In the drawings, like reference numerals have been used to designate identical elements. In describing the disclosed two-phase admixtures and methodology, the following terms have been used in the description.

The term "bio-identical hormone" refers to hormones that are chemically and structurally identical to those humans naturally produce and are derived from plant sources by Pharmaceutical manufacturers.

The term "Bi-Est" refers to a combination of estradiol and estriol in a specific proportion. A preferred proportion has an upper range of 80 percent by weight estradiol to 20 percent by weight estriol and a lower range of 20 percent by weight estradiol to 80 percent by weight estriol.

The term "mg" refers to the standard abbreviation for milligram, a metric unit of weight. The term "mL" refers to the standard abbreviation for milliliter, a metric unit of volume. The term 'nanoparticle' or "nanoparticles" refers to microscopic particles with at least one dimension less than 100 nanometers.

The term "drop" or "droplet" refers to a volume of liquid equal to 0.05 mL. This is the standard amount of liquid in a drop produced by the orifice reducer 104.

The term "wt %" refers to an abbreviation for weight percent.

The term "vol %" refers to an abbreviation for volume percent.

The term "admixture" or "combination" refer to a material composed of one or more separate ingredients or components.

The term "liquid phase" or "excipient carrier oil" or "liquid excipient carrier oil" refers to a miscible liquid solution comprising one or more of the excipient carrier oils listed in Table A—ESSENTIAL OILS OF PARTICULAR UTILITY IN EXCIPIENT CARRIER OIL COMPOSITIONS.

The term "solid phase" or "solid bio-identical hormone" or "solid bio-identical hormone formulation" refers to a solid comprising one or more of Bi-Est, progesterone, testosterone, and dehydroepiandrosterone.

The term "two-phase admixture" or "two-phase admixtures" or "two-phase bio-identical hormone admixture"

refers to a combination of one or more of the liquid phase components combined with one or more of the solid phase components in a specifically prescribed combination.

The term "appropriate laboratory container" refers to laboratory glassware designed to aid in the quantitative measurement of liquid volumes such as volumetric flasks.

The term "appropriate application container" refers to the dispensing bottle body 102 combined with the orifice reducer 104 and dispensing cap 100 and, while in storage, the sealing cap 200.

The term "first pass effect" refers to the mechanism of hormone metabolism that occurs with oral administration of a hormone. This mechanism is as follows: the hormone is absorbed from the intestinal tract and then travels directly to the liver. In the liver a substantial percentage of the administered hormone is immediately metabolized thus becoming ineffective for having any hormonal effect in the body. Another portion of that administered hormone is not metabolized, and does then pass into general circulation to have hormonal effects as it circulates throughout the body.

Unlike all other formulations used for hormone replacement therapy, the two-phase bio-identical hormone admixture disclosed herein is composed of two distinct phases, a solid and a liquid. It is common for other formulations to be composed of a solid, a semi-solid, a gel, a cream or a liquid. To achieve these single phase formulations additional components are introduced to promote the final single phase form. For example, ovarian and adrenal steroid hormones are sparingly soluble in lipophilic media; hence, it is necessary to introduce various strong solvents into the mixture to accomplish hormone solubility. These strong solvents have toxic potential, as evidenced in the scientific medical literature (for example, Kevin C. Wilson, M D; Christine Reardon, M D; Arthur C. Theodore, M D; and Harrison W. Farber, M D, FCCP; "Propylene Glycol Toxicity: A Severe Iatrogenic Illness in ICU Patients Receiving IV Benzodiazepines"; CHEST Journal, September 2005, Volume 128, No. 3, pages 1674-1681). Another beneficial aspect of the two-phase bio-identical hormone admixtures and methodology disclosed herein is to eliminate such localized application site irritation.

The bio-identical hormone admixture is composed of two distinct phases. One phase is a liquid composed of one or more excipient carrier oils as listed in Table A. In previous teachings (U.S. application Ser. No. 15/944,842 now U.S. Pat. No. 10,285,998 B1 and U.S. application Ser. No. 16/355,935—the disclosures of which are incorporated by reference in their entirety) the number of pharmacological oils was strictly limited by prior research and available physical property data on oil viscosity. In the intervening two years, new data has become available that has greatly expanded the number of common oils that are candidates for this pharmacological application. Examples of common oils now considered available as excipient carrier oils include olive oil, peanut oil, and corn oil among others. Additionally, capital investments in steam distillation plants and equipment have greatly expanded the number of the more rare oils that are candidates for this excipient carrier application due to increased availability and decreased cost. Examples of the more rare oils now considered available as excipient carrier oils include almond oil, marula oil, and sea buckthorn oil among others. A more comprehensive list of both common and rare essential oils which are currently available as components of excipient carrier oils is presented in Table A.

The most appropriate way to define the composition of the two-phase bio-identical hormone admixture is in terms of the distinct phases. The liquid phase is comprised of one or more of the excipient carrier oils listed in Table A.

Based upon new viscosity data, a number of single component liquid phase excipient carrier oils have been discovered. An exemplary preferred case is that of 100% olive oil.

No preparation is required to formulate a single component liquid phase excipient carrier oil.

Based upon further research, a number of binary (two) component liquid phase excipient carrier oils have been discovered. An exemplary preferred case is that of 50 volume percent (50 vol %) coconut oil and 50 volume percent (50 vol %) sunflower oil.

An exemplary preferred method of preparation of a specific excipient carrier oil mixture composed of two excipient carrier oils as components as listed above would include the following steps:
 (1) Measure out 50 mL of coconut oil.
 (2) Measure out 50 mL of sunflower seed oil.
 (3) Combine the above amounts of coconut oil and sunflower seed oil in an appropriate laboratory container (like a 100 mL volumetric flask).
 (4) Agitate well to insure complete mixing.
 (5) As there will be some volume loss due to mixing, add equal amounts of coconut oil and sunflower seed oil up to the 100 mL flask mark.
 (6) Agitate well to insure complete mixing.
 (7) Repeat steps (5) and (6) until no change in volume due to mixing is observed. The coconut oil concentration is 50.0 volume percent and the sunflower oil component is 50.0 volume percent.

Finding combinations of three or more excipient carrier oils to achieve the desired viscosity is difficult, but a particular combination of oils was discovered, via extensive experimentation, which achieves the final mixture viscosity that is essential to providing drops of a specific volume of the two-phase admixture using the orifice reducer 104. This exemplary preferred liquid phase contains jojoba oil, evening primrose oil, and borage seed oil, where the major component is jojoba oil in which the composition can range from 90.0 volume percent (90.0 vol %) to 96.0 volume percent (96.0 vol %), the evening primrose oil composition can range from 2.5 volume percent (2.5 vol %) to 6.5 volume percent (6.5 vol %), and the borage seed oil composition can range from 1.5 volume percent (1.5 vol %) to 3.5 volume percent (3.5 vol %).

An exemplary preferred method of preparation of a specific excipient carrier oil mixture having jojoba oil, evening primrose oil, and borage seed oil as components in specified amounts would include the following steps:
 (1) Measure out 6.3 mL of evening primrose oil.
 (2) Measure out 3.4 mL of borage seed oil
 (3) Combine the above amounts of evening primrose oil and borage seed oil in a appropriate laboratory container (like a100 mL volumetric flask)
 (4) Add jojoba oil up to slightly less than the 100 mL flask mark.
 (5) Agitate well to insure complete mixing.
 (6) Add further jojoba oil up to the 100 mL flask mark.
 (7) Agitate further to insure complete miscibility. The evening primrose oil concentration is 6.3 volume percent, the borage seed oil concentration is 3.4 volume percent, and the jojoba oil component is 90.3 volume percent.

The solid phase is comprised of one or more bio-identical hormones of Bi-Est, progesterone, testosterone, and dehydroepiandrosterone (DHEA). The composition of Bi-Est is composed of estradiol and estriol combined in a ratio that has a preferred upper range from between 20 weight percent (20 wt %) estradiol to 80 weight percent estriol (80 wt %) and a preferred lower range of 80 weight percent (80 wt %) estradiol to 20 weight percent (20 wt %) estriol. Of this combined mixture of estradiol and estriol, the concentration in the final two-phase bio-identical hormone admixture (combined solid and liquid phases) ranges between 5 mg per mL and 80 mg per mL. The other solid bio-identical hormones are prepared with preferred concentrations in the final two-phase bio-identical hormone admixture as follows:

| | |
|---|---|
| Progesterone | 5 mg/mL to 200 mg/mL |
| DHEA | 5 mg/mL to 200 mg/mL |
| Testosterone | 5 mg/mL to 200 mg/mL |

Ordinarily, the components of Bi-Est along with progesterone, testosterone, and dehydroepiandrosterone are available as coarse powders. However, recent advances have now made the above listed hormones available in nanoparticles form. For example, U.S. Pat. No. 6,623,761 B2 teaches how to prepare progesterone and testosterone in nanoparticle form. "Cryochemical Synthesis of Polymorphous Nanostructures of a Steroid Neurohormone," (*Molecules*, August 2017, Volume 22, No. 8, p. 1378) teaches how to prepare dehydroepiandrosterone in nanoparticles form. In chapter 6 of Nanoparticles for Dermal and Transdermal Drug Delivery by O. Uchechi, J. Ogbonna, and A. Attama (Jul. 24, 2014) teaches how to prepare estradiol in nanoparticle form. And, the U.S. application publication US20160120794 A1 teaches how to prepare estriol in nanoparticle form. The advantage of using the solid phase bio-identical hormones in nanoparticle form is that when combined in the two-phase admixture the admixture can be subjected to agitation such that the nanoparticles form a long-term stable dispersion making the preparation for application much easier and also increases the precision with which drops of the two-phase admixture can be produced.

An exemplary preferred method for compounding the two-phase bio-identical hormone admixture starts with the preparation of the liquid phase as indicated above. Depending upon the prescription for the two-phase bio-identical hormone admixture the liquid phase could have one or more excipient carrier oil components. As an example, if the final volume of two-phase bio-identical hormone admixture is to be 100 mL, then the appropriate amount of a solid phase bio-identical hormone (as either a coarse powder or nanoparticle preparation) would be added to an appropriate vessel, like a 100 mL volumetric flask, and the liquid phase, just prepared, would be added to bring the total volume up to 100 mL. Hence, as a further example, if the concentration of a solid phase bio-identical hormone is prescribed to be 50 mg per mL, then 5.0 grams (or equivalently 5000 mg) of the hormone would be added to the 100 mL volumetric flask and the liquid phase would be added to bring the total volume to 100 mL. The above procedure for preparing the two-phase bio-identical hormone admixture is most appropriately carried out by a compounding pharmacist.

However, having a prescription filled by a compounding pharmacist is not nearly as convenient as going to the corner pharmacy. To enable filling a prescription for the two-phase bio-identical hormone admixture by a regular pharmacist, it is possible to prepare various formulations of the two-phase bio-identical hormone admixture in advance. Just as various drugs are prepared in several strengths, the two-phase bio-identical hormone admixture can be prepared in various strengths of hormones. For single hormone formulations of progesterone, testosterone and dehydroepiandrosterone, providing the normal prescribed doses can be effectively enabled by providing one or more different concentrations of hormones. Table B—DISCRETE TWO-PHASE BIO-IDENTICAL HORMONE COMBINATIONS shows a combination of three concentrations of hormones. These combinations are:
 1. Bio-identical hormone concentration is 50 mg/mL.
 2. Bio-identical hormone concentration is 100 mg/mL.
 3. Bio-identical hormone concentration is 150 mg/mL.

For single hormone formulations of progesterone and dehydroepiandrosterone, the daily prescribed amount is in the range of 10 mg to 150 mg. By providing pre-made two-phase bio-identical hormone admixtures with concentrations of hormone of 50 mg/mL (2.5 mg per drop), 100 mg/mL (5 mg per drop) and 150 mg/mL (7.5 mg per drop) a wide range of doses can be prescribed. For example, for a minimum prescribed dose of 10 mg per day, 2 drops per arm of the 50 mg/mL formulation (total 10 mg) provides the required dose. As a further example, for a maximum prescribed dose of 150 mg per day, 10 drops per arm once a day (total 150 mg) or 5 drops per arm twice a day (total 150 mg) of the 150 mg/mL formulation provides the required dose. Daily doses between the usual minimum and usual maximum as noted above can be easily prescribed in terms a specified bio-identical hormone admixture concentration, the of the number of drops of said admixture, the number of application sites and the number of times per day application is carried out. Ideally, the hormone formulations above would be prepared with hormones in nanoparticle form such that agitation would produce long-term stable dispersions of the hormones in the excipient carrier oil.

For testosterone, the daily prescribed amount is in the range of 50 mg to 150 mg. By providing pre-made two-phase bio-identical hormone admixtures with concentrations of hormone of 50 mg/mL (2.5 mg per drop), 100 mg/mL (5 mg per drop) and 150 mg/mL (7.5 mg per drop), again, a wide range of doses can be prescribed. For example, for a minimum prescribed dose of 50 mg per day, 5 drops per arm of the 100 mg/mL formulation (total 50 mg) provides the required dose. As a further example, for a maximum prescribed dose of 150 mg per day, 10 drops per arm once a day (total 150 mg) or 5 drops per arm twice a day (total 150 mg) of the 150 mg/mL formulation provides the required dose. Daily doses between the usual minimum and usual maximum as noted above can be easily prescribed in terms a specified bio-identical hormone admixture concentration, the number of drops of said admixture, the number of application sites and the number of times per day application is carried out. Ideally, the testosterone formulations above would be prepared with testosterone in nanoparticle form such that agitation would produce long-term stable dispersions of the testosterone in the excipient carrier oil.

Providing the pre-made two-phase bio-identical hormone admixture for Bi-Est is more complicated because Bi-Est contains both estradiol and estriol. For Bi-Est, four hormone concentrations are necessary to allow a wide range doses to be prescribed. Table C—DISCRETE TWO-PHASE BIO-IDENTICAL HORMONE COMBINATIONS lists these four concentrations of Bi-Est. These combinations are:
 1. Total hormone concentration is 05 mg/mL with 80 wt % Estradiol and 20 wt % estriol.
 2. Total hormone concentration is 05 mg/mL with 20 wt % Estradiol and 80 wt % estriol.
 3. Total hormone concentration is 80 mg/mL with 80 wt % Estradiol and 20 wt % estriol.

4. Total hormone concentration is 80 mg/mL with 20 wt % Estradiol and 80 wt % estriol.

The most common prescribed amount of Bi-Est is approximately 2.5 mg per day. Using the prepared 80 wt % Estradiol @ 05 mg/mL Total Hormones formulation, prescribing 6 drops per arm once a day achieves a 2.4 mg per day dose (an amount very close to the required dose). Other prescribed daily doses are easily prescribed in terms a specified bio-identical hormone admixture concentration, the number of drops of said admixture, the number of application sites and the number of times per day application is carried out. Ideally, the hormone formulations above would be prepared with hormones in nanoparticle form such that combining agitation would produce long-term stable dispersions of the hormones in the excipient carrier oil.

Having available pre-made, pharmacy-ready two-phase bio-identical hormone admixtures of a small number of concentrations of solid bio-identical hormone allows a physician to prescribe an pharmaceutically effective dosage to a patient based upon a specific concentration of hormone in the pharmacy-ready two-phase admixture, the number of drops to apply of the two-phase admixture, the number of application sites and the temporal frequency.

The self-application of the two-phase bio-identical hormone admixture of excipient carrier oil and solid bio-identical hormone is made straight-forward by the incorporation of an orifice reducer 104 which may have one of several different diameters. The determination of a diameter which will dispense a drop having a known and constant volume depends upon several factors. A major factor is the fluid viscosity. Pure component fluids like olive oil, corn oil, sunflower seed oil, jojoba oil, evening primrose oil, or borage seed oil are Newtonian fluids where their viscosity is only a function of temperature. Also a mixture of jojoba oil, evening primrose oil, and borage seed oil (the components of an exemplary excipient carrier oil) is a Newtonian fluid. The viscosity of the excipient carrier oil will depend on the volumetric concentration of the components and can be considered to be constant for a specific mixture. Also being a Newtonian fluid, the viscosity of the exemplary excipient carrier oil does not change in response to agitation. It should be noted that combining jojoba oil, evening primrose oil, and borage seed oil (the exemplary excipient carrier oil) results in a fluid having a viscosity somewhat less than that of jojoba oil, but greater than either evening primrose oil or borage seed oil. Hence, by changing the relative concentrations of the components that make up the exemplary excipient carrier oil, the viscosity of the mixture can be adjusted to a value where liquid flow and mixing properties are favorable. However, the addition of a solid bio-identical hormone to the excipient carrier oil turns the resulting two-phase bio-identical hormone admixture into a non-Newtonian fluid where the agitation history influences the viscosity of the two-phase bio-identical hormone admixture. Note that the use of solid bio-identical hormones in nanoparticle form provides a two-phase admixture dispersion with nearly exact Newtonian fluid properties that have long-term stability. Hence, to obtain droplets of consistent volume and constant solid phase content (when the two-phase admixture is prepared from solid hormones in coarse powder form) from the orifice reducer 104 the temperature of the two-phase admixture, the composition of the two-phase admixture, and the agitation history of the two-phase admixture must remain relatively uniform. Considerable experimentation has allowed a determination as to the appropriate diameter of the orifice reducer 104 to get a dispensed drop of a specific volume having specific solid phase content for a specific two-phase bio-identical hormone admixture and agitation history.

An exemplary preferred method of self-application of the two-phase bio-identical hormone admixture is as follows. After the physician prescribes the two-phase bio-identical hormone admixture, the two-phase bio-identical hormone admixture is prepared by a regular pharmacist or a compounding pharmacist; subsequently, the regular pharmacist or a compounding pharmacist installs the prescribed orifice reducer 104 diameter, installs the dispensing cap 100, and then installs the sealing cap 200 which fits over the previously installed two orifice reducer 104 and the dispensing cap 100. The patient agitates the dispensing bottle 101 according to instructions, removes the sealing cap 200, and allows the prescribed number of drops of two-phase bio-identical hormone admixture to be applied to one forearm or both forearms as prescribed. Both forearms are then rubbed together allowing the two-phase bio-identical hormone admixture to be absorbed into the skin over a short period of time. This is repeated at prescribed time intervals, frequently either once or twice a day. Alternatively, a second exemplary preferred method of self-application would be to dispense the two-phase bio-identical hormone admixture to one or both of the inner thighs rubbing the two-phase bio-identical hormone admixture into the skin. Other obvious areas of application are the abdomen, outer thighs, outer shoulders and mucous membranes.

These methods of application are advantaged in that:
(1) The greater surface area of application of the two-phase bio-identical hormone admixture, which is very large compared to transdermal patches, reduces irritation due to reduced localized active pharmaceutical hormone concentration,
(2) The actual application site can be varied even further reducing the possibility of application site irritation,
(3) Rubbing to administer the two-phase bio-identical hormone admixture generates shear force, pressure, and heat by friction which aids in the adsorption of the two-phase formulation into the skin, and
(4) Does not require penetration enhancers to promote diffusion into the skin.

Other advantages of the two-phase bio-identical hormone admixture and these methods of application include:
(1) Does not require solvents to dissolve the active pharmaceutical solid phase hormones thus eliminating any toxic exposure from the solvents,
(2) Does not require a visit to a medical facility,
(3) Convenient for frequent doses,
(4) Just the appropriate dosage of the two-phase bio-identical hormone admixture can be administered to obtain the appropriate therapeutic concentration of replacement hormones in the body thereby reducing the possibility of adverse side effects.

Of further note, clinical trials are in progress and ongoing for the two-phase admixtures disclosed herein.

It will be apparent to those skilled in the art that various modifications and variations can be made to the two-phase admixtures and methodology disclosed herein. Thus, it is intended that the present two-phase admixtures and methodology cover such modifications and variations, provided they come within the scope of the appended claims and their equivalents.

The disclosure of all publications cited above is expressly incorporated herein by reference in their entireties to the same extent as if each were incorporated by reference individually.

TABLE A

ESSENTIAL OILS OF PARTICULAR UTILITY IN EXCIPIENT CARRIER OIL COMPOSITIONS

| Pharmacological Oil | Origin |
| --- | --- |
| Almond Oil (*Prunus dulcis*) | Extract from seeds of the cultured *Amygdalus communis* that originally grew in central and southwest Asia, now widely found in California. |
| Apricot Kernel Oil (*Prunus armeniaca*) | Extract from apricot kernels of the apricot tree which originated in Western Asia (Armenia) or China. |
| Apricot Oil | Extract from the pulp of the apricot tree which originated in Western Asia (Armenia) or China. |
| Argan Oil | Extract from kernels of the argan tree (*Argania spinosa L.*) that is endemic to Morocco. |
| Avocado Oil | Extract from the pulp of the avocado fruit from the avocado tree which originated in Mexico and Central America. |
| Baobab Oil | Extract from seeds of the baobab tree (*Adansoniadigitata*) which is an indigenous species found throughout the hot, arid regions of the African continent. |
| Black Cumin Oil | Extract from seeds of *Nigella satiya*, a plant native to southwest Asia. |
| Borage Seed Oil | Extract from seeds of the *Borago officinalis* plant. |
| Canola oil | Extract of from a variety of rapeseed that is low in erucic acid from of any of several cultivars of the plant family *Brassicaceae*. |
| Caprylic/Capric Triglyceride | Extract from the kernel or meat of matured coconut. |
| Carrot Seed Oil | Derived from the dried seeds of the *Daucus carota* botanical, more commonly known as the Wild Carrot or "Queen Anne's Lace". |
| Castor Seed Oil (*Ricinus communis*) | Extract from seeds of the castor plant which is indigenous to the southeastern Mediterranean Basin, Eastern Africa, and India. |
| Coconut Oil | Obtained by expression from the dried inner flesh of the coconut, *Cocos nucifera*. |
| Coconut, fractionated oil | Obtained by heating coconut oil above its melting point, and upon cooling, the solid fraction of the oil is separated from the liquid. |
| Corn Oil | Extract from the germ of corn (maize). |
| Evening Primrose Oil | Extract from the plant *Oenothera biennis* which is one of many species of the genus *Oenothera* found in North America. |
| Grapeseed Oil | Extract of the pulverized kernels of wine-producing grapes (*Vitis vinifera*). |
| Hemp Seed Oil | Extract from varieties of *Cannabis sativa* that do not contain significant amounts of tetrahydrocannabinol (THC). |
| Jojoba Oil | Extract of the seeds of the *Simmondsia chinensis* plant commonlyfound growing in the desert southwest of the US. |
| Macadamia Nut Oil | Extract from the ripe seeds of *Macadamia integrifolia* which is native to Australia and currently found in Hawaii. |
| Marula Oil | Extract of the kernels (nuts) of the fruits of the Marula trees (*Sclerocarya birrea*) which are native to parts of southern Africa. |
| Olive Oil | Extract of the fruit of the olive tree widely cultivated in Mediterranean region. |
| Palm Oil | Extract of the mesocarp (reddish pulp) of the fruit of the oil palms of African or cultivated origin. |
| Peanut Oil | Extract from the edible seeds of the peanut plant. |
| Pumpkin Seed Oil | Extract from the seeds of a pumpkin or *Cucurbita maxima*. |
| Rosehip Oil | Extract from the fruit and seeds of the rose plant (*Rosa canina*). |
| Safflower Oil | Extract from the flowering annual plant, *Carthamus tinctoris*, which is native to parts of Asia and Africa. |
| Sea Buckthorn Oil | Extract from the berries, leaves and seeds of the sea buckthorn plant (*Hippophae rhamnoides*), which is a small shrub that grows at high altitudes in the northwest Himalayan region. |
| Sesame Oil | Extract from the raw seeds of the Sesame plant widely cultivated through the world. |
| Sesame Seed Oil | Extract from the toasted seeds of the Sesame plant widely cultivated through the world. |
| Shea Butter Oil | Extract from the nut of the fruit from the Karite tree grown in Ghana, Mali, Burkina Faso and other Savanna Grasslands of West Africa. |
| Squalene | Extract of shark liver oil and also vegetable sources such as amaranth seed, rice bran, wheat germ, and olives |
| Sunflower Oil | Extract of the non-volatile oil pressed from the seeds of sunflower (*Helianthus annuus*). |
| Sunflower Oil (High Oleic) | Extract from sunflower seeds that have been conventionally bred to be high in oleic acid. |
| Tamanu Oil | Extract from nuts of either the *Calophyllum inophyllum* (usually) or the *Calophyllum tacamahaca* (ati), tropical trees. |
| Vitamin Oil (D-alpha Tocopherol) | Extract from wheat germ oil; most natural vitamin E supplements are now derived from vegetable oils, usually soybean oil. |
| Walnut oil | Extract from walnuts, *Juglans regia*. |

TABLE B

DISCRETE TWO-PHASE BIO-IDENTICAL HORMONE COMBINATIONS

FOR PROGESTERONE, TESTOSTERONE AND DEHYDROEPIANDROSTERONE

| DROPS | HORMONE CONCEN-TRATION 50 mg/mL | HORMONE CONCEN-TRATION 100 mg/mL | HORMONE CONCEN-TRATION 150 mg/mL |
|---|---|---|---|
| 1 | 2.5 mg | 5.0 | 7.5 |
| 2 | 5.0 mg | 10.0 | 15.0 |
| 3 | 7.5 mg | 15.0 | 22.5 |
| 4 | 10.0 mg | 20.0 | 30.0 |
| 5 | 12.5 mg | 25.0 | 37.5 |
| 6 | 15.0 mg | 30.0 | 45.0 |
| 7 | 17.5 mg | 35.0 | 52.5 |
| 8 | 20.0 mg | 40.0 | 60.0 |
| 9 | 22.5 mg | 45.0 | 67.5 |
| 10 | 25.0 mg | 50.0 | 75.0 |

1 DROP = 0.05 mL

TABLE C

DISCRETE TWO-PHASE BIO-IDENTICAL HORMONE COMBINATIONS FOR BI-EST

| DROPS | estradiol dose mg | estriol dose mg | estradiol dose mg | estriol dose mg |
|---|---|---|---|---|
| | 80 Wt % Estradiol @ 05 mg/mL Total Hormones | | 80 Wt % Estradiol @ 80 mg/mL Total Hormones | |
| 1 | 0.20 | 0.05 | 3.20 | 0.80 |
| 2 | 0.40 | 0.10 | 6.40 | 1.60 |
| 3 | 0.60 | 0.15 | 9.60 | 2.40 |
| 4 | 0.80 | 0.20 | 12.80 | 3.20 |
| 5 | 1.00 | 0.25 | 16.00 | 4.00 |
| 6 | 1.20 | 0.30 | 19.20 | 4.80 |
| 7 | 1.40 | 0.35 | 22.40 | 5.60 |
| 8 | 1.60 | 0.40 | 25.60 | 6.40 |
| | 20 Wt % Estradiol @ 05 mg/mL Total Hormones | | 20 Wt % Estradiol @ 80 mg/mL Total Hormones | |
| 1 | 0.05 | 0.20 | 0.80 | 3.20 |
| 2 | 0.10 | 0.40 | 1.60 | 6.40 |
| 3 | 0.15 | 0.60 | 2.40 | 9.60 |
| 4 | 0.20 | 0.80 | 3.20 | 12.80 |
| 5 | 0.25 | 1.00 | 4.00 | 16.00 |
| 6 | 0.30 | 1.20 | 4.80 | 19.20 |
| 7 | 0.35 | 1.40 | 5.60 | 22.40 |
| 8 | 0.40 | 1.60 | 6.40 | 25.60 |

1 drop = 0.05 mL

What is claimed is:

1. A pharmaceutical two-phase bio-identical hormone admixture comprising a solid bio-identical hormone comprised of one or more of Bi-Est, progesterone, testosterone and dehydroepiandrosterone (DHEA) and an excipient carrier oil comprised of one or more of the excipient carrier oils listed in Table A.

2. The pharmaceutical two-phase bio-identical hormone admixture of claim 1, wherein the solid bio-identical hormone is said Bi-Est with an overall concentration of said Bi-Est in said admixture of between is 5 mg per mL and 80 mg per mL.

3. The pharmaceutical two-phase bio-identical hormone admixture of claim 2, wherein said two-phase bio-identical hormone admixture is a topical dermatological formulation.

4. The pharmaceutical two-phase bio-identical hormone admixture of claim 3, wherein said topical dermatological formulation is applied to male or female human skin, or male or female human mucous membranes.

5. The pharmaceutical two-phase bio-identical hormone admixture of claim 1, wherein the solid bio-identical hormone is said dehydroepiandrosterone (DHEA) with an overall concentration of said dehydroepiandrosterone (DHEA) in said admixture of between 5 mg per mL and 200 mg per mL.

6. The pharmaceutical two-phase bio-identical hormone admixture of claim 5, wherein said two-phase bio-identical hormone admixture is a topical dermatological formulation.

7. The pharmaceutical two-phase bio-identical hormone admixture of claim 6, wherein said topical dermatological formulation is applied to male or female human skin or male or female human mucous membranes.

8. The pharmaceutical two-phase bio-identical hormone admixture of claim 1, wherein the solid bio-identical hormone is said progesterone with an overall concentration of said progesterone in said admixture of between 5 mg per mL and 200 mg per mL.

9. The pharmaceutical two-phase bio-identical hormone admixture of claim 8, wherein said two-phase bio-identical hormone admixture is a topical dermatological formulation.

10. The pharmaceutical two-phase bio-identical hormone admixture of claim 9, wherein said topical dermatological formulation is applied to male or female human skin or male or female human mucous membranes.

11. The pharmaceutical two-phase bio-identical hormone admixture of claim 1, wherein the solid bio-identical hormone is said testosterone, wherein the overall concentration of said testosterone in said admixture is between 5 mg per mL and 200 mg per mL.

12. The pharmaceutical two-phase bio-identical hormone admixture of claim 11, wherein said two-phase bio-identical hormone admixture is a topical dermatological formulation.

13. The pharmaceutical two-phase bio-identical hormone admixture of claim 12, wherein said topical dermatological formulation is applied to male or female human skin or male or female human mucous membranes.

* * * * *